United States Patent [19]

Newkirk

[11] Patent Number: 4,883,707

[45] Date of Patent: Nov. 28, 1989

[54] HIGH LOFT NONWOVEN FABRIC

[75] Inventor: David D. Newkirk, Greer, S.C.

[73] Assignee: James River Corporation, Richmond, Va.

[21] Appl. No.: 184,228

[22] Filed: Apr. 21, 1988

[51] Int. Cl.⁴ .......................... B32B 5/26; B32B 7/10; B32B 31/26

[52] U.S. Cl. .................................... 428/219; 156/290; 156/308.2; 428/286; 428/287; 428/288; 428/296; 428/298; 428/302; 428/340; 428/360; 428/362; 428/370; 604/370; 604/372; 604/378

[58] Field of Search ............... 428/219, 288, 296, 302, 428/340, 360, 362, 370; 156/290, 308.2

[56] References Cited

U.S. PATENT DOCUMENTS

| | | |
|---|---|---|
| 4,041,951 | 8/1977 | Sanford . |
| 4,391,869 | 7/1983 | Cook et al. . |
| 4,548,856 | 10/1985 | Ali Khan et al. . |
| 4,652,484 | 3/1987 | Shiba et al. . |

FOREIGN PATENT DOCUMENTS 2127865A  4/1984  United Kingdom .

OTHER PUBLICATIONS

Mizutani, "Designing Japanese Diapers Becomes a Growing Concern", Nonwoven World, Nov. 1987.

Pirkkanen, "Multi-Layer Nonwovens for Coverstock, Medical and Other End Uses", Nonwovens World, Nov. 1987.

*Primary Examiner*—James C. Cannon

[57]  ABSTRACT

Disclosed are high loft nonwoven fabric composites, suitable for use as coverstock in absorbent personal care articles, that are composed of at least two carded webs of bicomponent thermoplastic resin fibers, wherein the fibers making up at least one web are at least in part flat-crimped bicomponent fibers. Also disclosed is a method of making such laminates by a process that involves thru-air bonding.

14 Claims, No Drawings

HIGH LOFT NONWOVEN FABRIC

BACKGROUND OF THE INVENTION

This invention relates to nonwoven fabrics. More particularly, the present invention relates to multilayer nonwoven fabric composites of thermoplstic resin fibers, wherein the fibers making up at least one layer are at least in part flat-crimped bicomponent fibers, and to a method for manufacturing such composites. The nonwoven fabric composites of the present invention are configured in such a way as to be especially useful as coverstock in absorbent articles such as disposable diapers and sanitary napkins.

Disposable diapers, sanitary napkins, and the like are generally composed of an impermeable outer covering, an absorbent layer, and an inner layer that—ideally—permits liquid to flow through it rapidly into the absorbent layer ("rapid strike through") but does not permit or at least does not facilitate re-transmission of liquid from the absorbent layer to the "baby" or "wearer" side of said inner layer ("resists rewet"). Said inner layer is referred to as coverstock, topsheet, or, in diaper applications, diaper liner. In addition to liquid transport properties, the coverstock must have sufficient strength to allow for converting it—that is, incorporating into the final product—on a diaper or other machine and for resistance to failure during vigorous movement by the user. On the other hand, while strength is essential, the coverstock should present a soft comfortable feel against the user's skin. Currently these somewhat conflicting requirements—for softness coupled with strength—have been met only imperfectly, for the most part by coverstock made from thin low basis weight (in the neighborhood of 20 grams per square yard) carded or spunbonded nonwoven fabrics.

It has been recognized that many aspects of coverstock performance could be substantially improved if the thickness, or caliper, of the coverstock fabric were increased. The subjective feel—softness and dryness—of diaper liner has become more important with the increased use of diapers by incontinent adults. Surface dryness generally can be improved by increasing the separation between the wearer's skin and the absorbent core of the diaper. Since this separation must be maintained during use of the diaper it is essential that the thick diaper liner maintain its caliper under some degree of compression loading. Thickness can be increased by increasing the basis weight of the coverstock and/or by decreasing the density thereof (that is, by making the coverstock more "lofty"). Increased thickness through loft should offer improved softness as well as improved surface dryness.

Many approaches have been suggested for producing thick diaper liner. For example, U.S. Pat. No. 4,041,951 teaches embossing nonwoven topsheet to increase its bulk, and U.S. Pat. No. 4,391,869 discloses limiting the amount of aqueous binder applied in the suction bonding of airlaid nonwoven fabric. More recently, the use of thru-air bonded bicomponent fiber structures have been investigated. One use of the thru-air technique is alluded to in an article entitled "Multi-layer Nonwovens for Coverstock, Medical, and other End Uses" by J. Pirkkanen in the November 1987 issue of "Nonwovens World". The reference discloses a multilayer nonwoven fabric having a basis weight of about 30 grams per square meter. U.S. Pat. No. 4,548,856 and U.K. patent application GB No. 2,127,865A disclose thru-air bonding procedures that involve the use of multibelt systems to form patterned nonwoven fabrics.

U.S. Pat. No. 4,652,484 assigned to Kao teaches that improved diaper liner will result from layered structure wherein the first layer is predominently comprised of 1-3 denier straight bicomponent fibers and the second layer is predominently comprised of sterically buckled (three-dimensional crimp) 1.5 to 6 denier bicomponent fibers. It is believed that what the patent refers to as "straight" fibers are actually flat-crimped fibers. The method used to bond this structure is not disclosed in detail. The diaper liner used in commercial MERRIES diapers, which are produced by Kao have a basis weight of approximately 30 grams per square yard. The examples of diaper liners according to the invention disclosed in U.S. Pat. No. 4,652,484 have basis weights of 35 grams per square yard. Thus the Kao structure suggests the need for a 50% increase in basis weight over conventional (20 grams per square yard) diaper liner. Also, the Kao patent teaches that optimum thickness and softness is achieved only if the structure is complicated by the use of sterically-buckled bicomponent fibers.

I have now unexpectantly found that diaper liner having properties of thickness, softness, and strength comparable to the Kao products can be manufactured using flat-crimped (rather than sterically-buckled) bicomponent fibers. Moreover, I can achieve such results at substantially reduced basis weights compared to the basis weights of comparable webs described by the Kao patent.

SUMMARY OF THE INVENTION

The nonwoven fabric provided by this invention is a high loft composite that has strength and softness sufficient to make it suitable for use as coverstock for diapers, sanitary napkins, and the like. The high loft coverstock of this invention is composed of a carded web layer comprising crimped thermoplastic fibers having an average denier of 3 or greater to which has been bonded a carded web layer comprising thermoplastic fibers having an average denier of 3 or less. Sufficient bicomponent fiber must be present so that bonding may be accomplished by a thru-air method in order to maximize retention of caliper, strength, and softness. In accordance with the present invention, the higher denier layer is substantially free of sterically-buckled fibers.

Another aspect of the present invention is a method for making high loft composite that comprises forming a first carded web comprising crimped thermoplastic fibers having an average denier of 3 or greater and having a basis weight in the range of from 5 through 20 grams per square yard, forming a second carded web comprising thermoplastic fibers having an average denier of 3 or less and having a basis weight in the range of from 5 through 20 grams per square yard, wherein each of said webs contains sufficient thermoplastic bicomponent fiber to provide for bonding within each said web layer and between said web layers, superimposing said second web onto said first web to form a layered structure, contacting said layered structure with a thru-air bonding surface having 25-60% open area, and causing heated air to pass through said bonding surface into and through said layered structure in order to effect bonding between the web layers.

DESCRIPTION OF THE PREFERRED EMBODIMENTS

Any type of thermoplastic bicomponent fibers can be used in the manufacture of the high loft nonwoven fabrics of this invention. For example, sheath/core, side-by-side, and other types of bicomponent fibers can be used. A variety of thermoplastic resin combinations is available. The fibers are generally crimped via typical textile means, for example a stuffer box method, to achieve a predominately two-dimensional or "flat" crimp. However, uncrimped bicomponent fibers may be used in the soft facing layer, as may be sterically-buckled fibers. However, contrary to the teachings of U.S. Pat. No. 4,652,484, three-dimensionally ("sterically") crimped fibers are not required to obtain a lofty fabric. In accordance with the present invention, sufficient loft can be obtained by the use of flat-crimped bicomponent fibers in the higher denier layer.

Currently preferred fibers according to the present invention are the composites wherein the bicomponent fibers in the carded web layers are selected from the group consisting of sheath/core fibers of the following resin combinations: polyethylene/polypropylene, polyethylene/polyester, polypropylene/polyester, and copolyester/polyester. Specific examples of such fibers are 1.7 and 3 denier polyethylene/polyester sheath/core fibers available from BASF CORPORATION as Products 1051 and 1050, respectively; 2 and 3 denier copolyester/polyester sheath/core fibers available from CELANESE FIBERS as Type 354; and 1.5 and 3 denier polyethylene/polypropylene sheath/core fibers available from CHORI AMERICA as Daiwabo NBF Type H.

High loft coverstock according to the present invention is generally composed of two layers: a soft facing layer and a lofty layer that is essential to the "wet" properties of the composite. However, more than two layers could be used if desired in order to engineer additional properties into the composite. Multiple layers are discussed in a similar context in the Pirkannen article cited hereinabove.

Neither the high denier lofty layer nor the low denier soft layer need be composed entirely of the bicomponent fibers. The desired balance of loft, softness, and strength determines the upper percent by weight of single component matrix fiber that can be added. Both loft and softness increase and strength decreases as matrix (single component) fiber is added. Addition of greater than 25–30% matrix fiber may reduce the strength to a level of concern for use as a traditional diaper topsheet. A hollow polyester fiber has been found to be a particularly useful hydrophobic matrix fiber to promote the retention of caliper under loading conditions.

The relative weights of the two layers in the composite will influence the balance of loft, softness, and strength. Softness is optimized when the low denier layer makes up more than 50% of the basis weight of the structure. Strength is optimized as the higher denier layer makes up more than 50% of the basis weight of the structure. Thus the optimum ratio between the high and low denier layer will be dependent on the needed level of softness and strength but can range from approximately 1:3 to 3:1.

The carded web layers as prepared have natural high loft. It is important not to destroy that natural loft in the process of bonding the two layers together. The preferred manner of bonding the low denier layer to the high denier layer is by "thru-air" bonding. In the thru-air bonding process, the web containing bicomponent fibers is exposed to air heated to a temperature such that the lower melting part, for example the sheath part, of the bicomponent fiber softens and begins to melt. Contact of this molten filament with a second filament will upon cooling form a bond. Contact between fibers can be achieved by the natural compression of gravity, the force of a moving stream of heated air against the fibers, and/or by a hold-down wire that puts a compressing force against the filaments to promote bonding.

In accordance with the present invention, it is preferred to operate in the absence of a hold-down wire. The heated air can be introduced into the web of bicomponent fibers in a very uniform way to maximize uniform bonding of filaments to each other. Alternatively the air can be introduced according to a pattern so that intermittent bonding is achieved in those areas of concentrated air flow. Thru-air pattern bonding is discussed in U.S. Pat. No. 4,548,856 and U.K. patent application 2,127,865A, the disclosures of which are incorporated herein by reference. Both of these references, however, appear to teach the use of hold-down wires.

Uniform air introduction according to the present invention is promoted if the wire or drum supported the web during air introduction is very open. Pattern bonding is promoted if the wire or drum supporting the web during air induction has a pattern of open and closed areas such that the closed areas made up a substantial portion of the total area of the wire or drum. It is believed that such a structure of intermittent bonding achieved by use of a wire or drum of reduced open area in the absence of a hold-down wire is responsible for the unexpected balance of loft, softness, and strength seen in the products of this invention.

The webs of this invention may be thru-air bonded by the use of bonding surfaces such as wires or drums that have approximately 25–60 percent open area. By "percent open area" is meant the fraction of the bonding surface that is open so that hot air can move from the heat source through the web of bicomponent fibers. A particularly useful way to produce the coverstock of this invention is to use a bonding drum having approximately 30–40% open area. Retention of high loft is maximized by not using a hold-down wire.

ILLUSTRATIVE EXAMPLES

In the examples that follow, the expression "gm/sqy" means "grams per square yard", the expression "gm/sqi" means grams per square inch, and the expression "psi" means "pounds per square inch". Basis weight was determined by measuring the weight of a known area of fabric. The result, reported as grams per square yard ("gm/sqy"), is the average of at least 4 measurements.

Following is a description of the test methods used to evaluate these products.

STRIP TENSILE STRENGTH

Strip tensile strength was evaluated by breaking a one inch by seven inch long sample generally following ASTM D1682-64, the One-Inch Cut Strip Test. The instrument cross-head speed was set at 5 inches per minute and the gauge length was set at 5 inches. The tensile strength in both the machine direction ("MD") and cross direction ("CD") was evaluated. The Strip Tensile Strength or breaking load, reported as grams per inch, is the average of at least 8 mesurements.

CALIPER (UNDER COMPRESSION)

Caliper was determined by measuring the distance between the top and the bottom surface of the sheet while the sheet was held under compression loading of 19 grams per square inch, 107 grams per square inch, or 131 grams per square inch. The result, reported in mils, is the average of 10 measurements.

STRIKE-THROUGH

Strike-Through was evaluated by a method similar to that described in U.S. Pat. Nos. 4,391,869 and 4,041,451. Strike-Through was measured as the time for 5 ml of synthetic urine solution placed in the cavity of the strike-through plate to pass through the Example Fabric into an absorbent pad. The result, reported in seconds, is generally the average of 4 tests.

SURFACE WETNESS

Surface Wetness was evaluated by a method similar to that described in U.S. Pat. Nos. 4,041,951 and 4,391,861. Surface Wetness, reported in grams, was evaluated by adding synthetic urine through the Example Fabric into the absorbent pad until the absorbent pad was nearly saturated. Thus the Example Fabric was wet at the beginning of the Surface Wetness test. For results denoted as Surface Wetness 1, the loading factor was slightly less than 4 (grams of synthetic urine per gram of absorbent sample). A uniform pressure loading of 0.5 psi was then applied and the procedure concluded as disclosed in the above patents. For results denoted as Surface Wetness 2, the loading factor was increased to slightly over 4 so the absorbent pad was saturated with synthetic urine. A uniform pressure loading of 1.0 psi was then applied and the procedure concluded as disclosed in the above patents. The result, reported in grams, is generally the average of 4 tests.

SOFTNESS

Softness was evaluated by an organoleptic method wherein an expert panel compared the surface feel of Example Fabrics with that of controls. Results are reported as a softness score with higher values denoting a more pleasing hand. Each reported value is for a single fabric test sample but reflects the input of several panel members.

Example 1

A carded web having a basis weight of 8 gm/sqy and composed of 75% 3.0 denier flat-crimped polyethylene/polyester sheath/core bicomponent fiber blended with 25% 5.5 denier hollow polyester fiber was laid on a moving belt. This high denier layer was overlaid with a carded web having a basis weight of 16 gm/sqy and consisting of 1.7 denier flat-crimped polyethylene/polyester sheath/core bicomponent fiber. The two-layered assembly was supported on a rotating bonding drum having 35% open area such that air heated to 130°–135° C. was blown through the assembly for an exposure time of approximately 13 seconds. The web was compressed together by the air velocity moving through the web into the patterned open areas of the bonding drum. No hold-down wire was used. The resulting composite nonwoven fabric according to this invention, which had a basis weight of 22 gm/sqy, had these properties:

The fabric has an MD Strip Tensile Strength of 1266 grams per inch and a CD Strip Tensile Strength of 222 grams per inch Its Caliper under compression was, at 19 gm/sqi, 55 mils, at 107 gm/sqi, 27 mils, and, at 131 gm/sqi, 27 mils.

Strike-Through was 1.6 seconds.

Surface Wetness 1 was 0.12 grams; Surface Wetness 2 was 0.30 grams.

The topside Softness rating was 88; bottomside Softness was 78.

EXAMPLE 2

A carded web having a basis weight of 12 gm/sqy and composed of 3.0 denier flat-crimped polyethylene/polyester sheath/core bicomponent fiber was laid on a moving belt. This high denier layer was overlaid with a carded web having a basis weight of 11 gm/sqy and consisting of 1.7 denier flat-crimped polyethylene/polyester sheath/core bicomponent fiber. The two-layered assembly was supported on a rotating bonding drum having 35% open area such that air heated to 128° C. was blown through the assembly for an exposure time of approximately 17 seconds. The web was compressed together by the air velocity moving through the web into the patterned open areas of the bonding drum. No hold-down wire was used. The resulting composite nonwoven fabric according to this invention, which had a basis weight of 23 gm/sqy, had these properties:

The fabric had an MD Strip Tensile Strength of 1112 grams per inch and a CD Strip Tensile Strength of 402 grams per inch.

Its Caliper under compression was, at 19 gm/sqi, 61 mils, at 107 gm/sqi, 37 mils and, at 131 gm/sqi, 35 mils.

Srike-Through was 0.9 seconds.

Surface Wetness 1 was 0.23 grams; Surface Wetness 2 was 0.16 grams.

The topside Softness rating was 80; bottomside Softness was 82.

EXAMPLE 3

A carded web having a basis weight of 17 gm/sqy and composed of 3.0 denier flat-crimped polyethylene/polyester sheath/core bicomponent fiber was laid on a moving belt. This high denier layer was overlaid with a carded web having a basis weight of 14.5 gm/sqy and consisting of 1.7 denier flat-crimped polyethylene/polyester sheath/core bicomponent fiber. The two-layered assembly was supported on a rotating bonding drum having 35% open area such that air heated to 130° C. was blown through the assembly for an exposure time of approximately 17 seconds. The web was compressed together by the air velocity moving through the web into the patterned open areas of the bonding drum. No hold-down wire was used. The resulting composite nonwoven fabric according to this invention, which had a basis weight of 31.5 gm/sqy, had these properties:

The fabric had an MD Strip Tensile Strength of 1405 grams per inch and a CD Strip Tensile Strength of 295 grams per inch.

Its Caliper under compression was, at 19 gm/sqi, 76 mils, at 107 gm/sqi, 45 mils and, at 131 gm/sqi, 45 mils.

Strike-Through was 0.8 seconds.

Surface Wetness 1 was 0.20 grams; Surface Wetness 2 was 0.56 grams.

The topside Softness rating was 85; bottomside Softness was 85.

EXAMPLE 4

A carded web having a basis weight of 10 gm/sqy and composed of 3.0 denier flat-crimped polyethylene/polyester sheath/core bicomponent fiber was laid on a moving belt. This high denier layer as overlaid with a carded web having a basis weight of 10 gm/sqy and consisting of 1.7 denier flat-crimped polyethylene/polyester sheath/core bicomponent fiber. The two-layered assembly was supported on a rotating bonding drum having 35% open area such that air heated to 129° C. was blown through the assembly for an exposure time of approximately 17 seconds. The web was compressed together by the air velocity moving through the web into the patterned open areas of the bonding drum. No hold-down wire was used. The resulting composite nonwoven fabric according to this invention, which had a basis weight of 20 gm/sqy, had these properties:

The fabric had an MD Strip Tensile Strength of 974 grams per inch and a CD Strip Tensile Strength of 208 grams per inch.

Its Caliper under compression was, at 19 gm/sqi, 44 mils, at 107 gm/sqi, 22 mils and, at 131 gm/sqi, 23 mils.

Strike-Through was 1.1 seconds.

Surface Wetness 1 was 0.15 grams; Surface Wetness 2 was 0.12 grams.

The topside Softness rating was 85; bottomside Softness was 80.

EXAMPLE 5

A carded web having a basis weight of 15 gm/sqy and composed of 3.0 denier flat-crimped polyethylene/polyester sheath/core bicomponent fiber was laid on a moving belt. This high denier layer was overlaid with a carded web having a basis weight of 8 gm/sqy and consisting of 1.7 denier flat-crimped polyethylene/polyester sheath/core bicomponent fiber. The two-layered assembly was supported on a rotating bonding drum having 35% open area such that air heated to 130° C. was blown through the assembly for an exposure time of approximately 17 seconds. The web was compressed together by the air velocity moving through the web into the patterned open areas of the bonding drum. No hold-down wire was used. The resulting composite nonwoven fabric according to this invention, which had a basis weight of 23 gm/sqy, had these properties:

The fabric had an MD Strip Tensile Strength of 1208 grams per inch and a CD Strip Tensile Strength of 318 grams per inch.

Its Caliper under compression was, at 19 gm/sqi, 60 mils, at 107 gm/sqi, 35 mils and, at 131 gm/sqi, 35 mils.

Strike-Through was 1.0 seconds. Surface Wetness 1 was 0.22 grams; Surface Wetness 2 was 0.44 grams.

The topside Softness rating was 85; bottomside Softness was 85.

EXAMPLE 6

A carded web having a basis weight of 8 gm/sqy and composed of 3.0 denier flat-crimped polyethylene/polyester sheath/core bicomponent fiber was laid on a moving belt. This high denier layer was overlaid with a carded web having a basis weight of 17 gm/sqy and consisting of 1.7 denier flat-crimped polyethylene/polyester sheath/core bicomponent fiber. The two-layered assembly was supported on a rotating bonding drum having 35% open area such that air heated to 129° C. was blown through the assembly for an exposure time of approximately 17 seconds. The web was compressed together by the air velocity moving through the web into the patterned open areas of the bonding drum. No hold-down wire was used. The resulting composite nonwoven fabric according to this invention, which had a basis weight of 25 gm/sqy, had these properties:

The fabric had an MD Strip Tensile Strength of 1425 grams per inch and a CD Strip Tensile Strength of 291 grams per inch.

Its Caliper under compression was, at 19 gm/sqi, 61 mils, at 107 gm/sqi, 36 mils and, at 131 gm/sqi, 38 mils.

Strike-Through was 1.0 seconds.

Surface Wetness 1 was 0.13 grams; Surface Wetness 2 was 0.33 grams.

The topside Softness rating was 92; bottomside Softness was 68.

EXAMPLE 7

A carded web having a basis weight of 11 gm/sqy and composed of 3.0 denier flat-crimped copolyester/polyester sheath/core bicomponent fiber was laid on a moving belt. This high denier layer was overlaid with a carded web having a basis weight of 6 gm/sqy and consisting of 2 denier flat-crimped copolyester/polyester sheath/core bicomponent fiber. The two-layered assembly was supported on a rotating bonding drum having 35% open area such that air heated to 130° C. was blown through the assembly for an exposure time of approximately 17 seconds. The web was compressed together by the air velocity moving through the web into the patterned open areas of the bonding drum. No hold-down wire was used. The resulting composite nonwoven fabric according to this invention, which had a basis weight of 17 gm/sqy, had these properties:

The fabric had an MD Strip Tensile Strength of 944 grams per inch and a CD Strip Tensile Strength of 329 grams per inch.

Its Caliper under compression was, at 19 gm/sqi, 30 mils, at 107 gm/sqi, 23 mils and, at 131 gm/sqi, 26 mils.

Strike-Through was 1.0 seconds.

Surface Wetness 1 was 0.10 grams.

The topside Softness rating was 15; bottomside Softness was 20.

EXAMPLE 8

A carded web having a basis weight of 15 gm/sqy and composed of a blend of 50% 3.0 denier flat-crimped copolyester/polyester sheath/core bicomponent fiber and 50% 5.5 denier hollow polyester matrix fiber was laid on a moving belt. This high denier layer was overlaid with a carded web having a basis weight of 6 gm/sqy and consisting of 2 denier flat-crimped copolyester/polyester sheath/core bicomponent fiber. The two-layered assembly was supported on a rotating bonding drum having 35% open area such that air heated to 160° C. was blown through the assembly for an exposure time of approximately 17 seconds. The web was compressed together by the air velocity moving through the web into the patterned open areas of the bonding drum. No hold down wire was used. The resulting composite nonwoven fabric according to this invention, which had a basis weight of 21 gm/sqy, had these properties:

The fabric had an MD Strip Tensile Strength of 1103 grams per inch and a CD Strip Tensile Strength of 325 grams per inch.

Its Caliper under compression was, at 19 gm/sqi, 77 mils, at 107 gm/sqi, 36 mils and, at 131 gm/sqi, 36 mils.

Strike-Through was 0.8 seconds.

Surface Wetness 1 was 0.14 grams.

The topside Softness rating was 45; bottomside Softness was 55.

EXAMPLE 9

A carded web having a basis weight of 15 gm/sqy and composed of a blend of 50% 3 denier flat-crimped copolyester/polyester sheath/core bicomponent fiber and 50% 5.5 denier hollow polyester matrix fiber was laid on a moving belt. This high denier layer was overlaid with a carded web having a basis weight of 9 gm/sqy and composed of a blend of 33% 1.5 denier polyester matrix fiber and 67% 2 denier flat-crimped copolyester/polyester sheath/core bicomponent fiber. The two-layered assembly was supported on a rotating bonding drum having 35% open area such that air heated to 160° C. was blown through the assembly for an exposure time of approximately 17 seconds. The web was compressed together by the air velocity moving through the web into the patterned open areas of the bonding drum. No hold-down wire was used. The resulting composite nonwoven fabric according to this invention, which had a basis weight of 24 gm/sqy, had these properties:

The fabric had an MD Strip Tensile Strength of 605 grams per inch and a CD Strip Tensile Strength of 153 grams per inch.

Its Caliper under compression was, at 19 gm/sqi, 85 mils, at 107 gm/sqi, 34 mils and, at 131 gm/qi, 33 mils.

EXAMPLE 10

A carded web having a basis weight of 16 gm/sqy and composed of 3 denier flat-crimped polyethylene/polypropylene sheath/core bicomponent fiber was laid on a moving belt. This high denier layer was overlaid with a carded web having a basis weight of 13 gm/sqy and composed of 1.5 denier flat-crimped polyethylene/polypropylene sheath/core bicomponent fiber. The two-layered assembly was supported on a rotating bonding drum having 35% open area such that air heated to 130°–132° C. was blown through the assembly for an exposure time of approximately 17 seconds. The web was compression together by the air velocity moving through the web into the patterned open areas of the bonding drum. No hold-down wire was used. The resulting composite nonwoven fabric according to this invention, which had a basis weight of 29 gm/sqy, had these properties:

The fabric had an MD Strip Tensile Strength of 2121 grams per inch and a CD Strip Tensile Strength of 664 grams per inch.

Its Caliper under compression was, at 19 gm/sqi, 42 mils, and, at 107 gm/sqi, 33 mils.

EXAMPLE 11

A carded web having a basis weight of 16 gm/sqy and composed of a blend of 50% 3 denier flat-crimped polyethylene/polypropylene sheath/core bicomponent fiber and 50% 2 denier polypropylene matrix fiber was laid on a moving belt. This high denier layer was overlaid with a carded web having a basis weight of 12 gm/sqy and composed of 1.5 denier flat-crimped polyethylene/polypropylene sheath/core bicomponent fiber. The two-layered assembly was supported on a rotating bonding drum having 35% open area such that air heated to 130° C. was blown through the assembly for an exposure time of approximately 17 seconds. The web was compressed together by the air velocity moving through the web into the patterned open areas of the bonding drum. No hold-down wire was used. The resulting composite nonwoven fabric according to this invention, which had a basis weight of 28 gm/sqy, had these properties:

The fabric had an MD Strip Tensile Strength of 1840 grams per inch and a CD Strip Tensile Strength of 281 grams per inch.

Its Caliper under compression was, at 19 gm/sqi, 49 mils, and, at 107 gm/sqi, 30 mils.

Comparative Example A (Diaper Liner from MERRIES Diaper)

Diaper Liner was removed from a MERRIES Diaper manufactured by Kao Corporation. This liner is believed to be produced by the method disclosed in U.S. Pat. No. 4,652,484. The composite nonwoven fabric, which had a basis weight of 30 gm/sqy, had these properties.

The fabric had an MD Strip Tensile Strength of 1257 grams per inch and a CD Strip Tensile Strength of 292 grams per inch.

Its Caliper under compression was, at 19 gm/sqi, 41 mils, and, at 107 gm/sqi, 18 mils.

Strike-Through was 1.4 seconds.

Surface Wetness 1 was 0.08 grams.

The topside Softness rating was 85.

Comparative Example B (Continental diaper liner)

Nonwoven fabric sold for diaper liner by James River Corporation, produced by the thermal calendering of a carded web of 2 denier polypropylene fiber, was analyzed. The nonwoven fabric, which had a basis weight of 20 gm/sqy, had these properties:

The fabric had an MD Strip Tensile Strength of 1500 grams per inch and a CD Strip Tensile Strength of 300 grams per inch.

Its Caliper under compression was, at 19 gm/sqi, 18 mils and, at 107 gm/sqi, 10 mils.

Strike-Through was 2.0 seconds.

Surface Wetness 1 was 0.11 grams; Surface Wetness 2 was 1.0 grams.

The topside Softness rating was 80.

From the above description, many variations in the composites and processes of this invention will be apparent to those skilled in the art. Such variations are within the scope of this invention as measured by the appended claims.

What is claimed is:

1. A nonwoven fabric having a basis weight in the range of 15–40 grams per square yard and suitable for use as coverstock that comprises
    a soft carded web layer consisting essentially of thermoplastic fibers having an average denier of 3 or less, and
    a lofty carded web layer consisting essentially of thermoplastic fibers having an average denier of 3 or greater,
wherein said webs contain sufficient thermoplastic bicomponent fiber to provide bonding within and between each of said web layers and wherein the thermoplastic bicomponent fiber in said lofty layer is flat-crimped.

2. A high loft coverstock according to claim 1 having a basis weight of less than 26 grams per square yard and having a caliper under a compression of 107 grams per square inch of at least 20 mils.

3. A high loft coverstock according to claim 2 that consists of two carded web layers wherein one or both of said layers comprises up to 50% by weight single component hydrophobic fibers.

4. A high loft coverstock according to claim 3 wherein the bicomponent fibers in said webs are selected from the group consisting of sheath/core fibers of the resin combination polyethylene/polypropylene, polyethylene/polyester, polypropylene/polyester, and copolyester/polyester.

5. A high loft coverstock according to claim 4 wherein the higher denier carded web has a basis weight in the range of from 5 through 20 grams per square yard and comprises a blend of a major portion of polyethylene/polyester sheath/core bicomponent fibers and a minor portion of hollow polyester fibers and the lower denier carded web has a basis weight in the range of from 5 through 20 grams per square yard and is comprised of polyethylene/polyester sheath/core bicomponent fibers.

6. A high loft coverstock according to claim 5 wherein the higher denier carded web has a basis weight of about 8 grams per square yard and consists of a blend of about 75% 3.0 denier flat-crimped polyethylene/polyester sheath/core bicomponent fibers and about 25% 5.5 denier hollow polyester fibers and the lower denier carded web has a basis weight of about 16 grams per square yard and consists of 1.7 denier flat-crimped polyethylene/polyester sheath/core bicomponent fibers.

7. A method for making high loft composite that comprises
forming a first carded web comprising crimped thermoplastic fibers having an average denier of 3 or greater and having a basis weight in the range of from 5 through 20 grams per square yard,
forming a second carded web comprising thermoplastic fibers having an average denier of 3 or less and having a basis weight in the range of from 5 through 20 grams per square yard,
wherein each of said webs contains sufficient thermoplastic bicomponent fiber to provide for bonding within each said web layer and between said web layers and wherein the thermoplastic bicomponent fiber in said lofty layer is flat-crimped,
superimposing said second web onto said first web to form a layered structure,
contacting said layered structure with a thru-air bonding surface having 25-60% open area, and
causing heated air to pass through said bonding surface into and through said layered structure in order to effect bonding between the web layers, wherein said heated air is passed through said layered structure in the absence of a hold-down wire.

8. A method as in claim 7 wherein said layered structure is contacted with the bonding surface in such a way that said heated air passes first into and through said second web and subsequently into and through said first web and finally exits through the bonding surface.

9. A method as in claim 8 wherein a bonding surface having 30-40% bonding area is employed.

10. A method as in claim 9 wherein one or both of said carded web layers comprises up to 50% by weight single component hydrophobic fibers.

11. A method as in claim 10 wherein the bicomponent fibers in said webs are selected from the group consisting of sheath/core fibers of the resin combinations polyethylene/polypropylene, polyethylene/polyester, polypropylene/polyester, and copolyester/polyester.

12. A method as in claim 11 wherein the higher denier carded web has a basis weight in the range of from 5 through 20 grams per square yard and is comprised of a blend of a major portion of polyethylene/polyester sheath/core bicomponent fibers and a minor portion of hollow polyester fibers and the lower denier carded web has a basis weight in the range of from 5 through 20 grams per square yard and is comprised of polyethylene/polyester sheath/core bicomponent fibers.

13. A method as in claim 12 wherein the higher denier carded web has a basis weight of about 8 grams per square yard and consists of a blend of about 75% 3.0 denier flat-crimped polyethylene/polyester sheath/core bicomponent fibers and about 25% 5.5 denier hollow polyester fibers and the lower denier carded web has a basis weight of about 16 grams per square yard and consists of 1.7 denier flat-crimped polyethylene/polyester sheath/core bicomponent fibers.

14. The product of the process of claim 7.

* * * * *